United States Patent [19]
Ghalili

[11] Patent Number: 5,106,299
[45] Date of Patent: Apr. 21, 1992

[54] DENTAL PROSTHESIS FOR USE WITH AN ORAL IMPLANT, AND METHOD OF INSTALLATION

[76] Inventor: Kambiz M. Ghalili, 200 Central Park South, New York, N.Y. 10019

[21] Appl. No.: 720,744

[22] Filed: Jun. 25, 1991

[51] Int. Cl.⁵ .............................................. A61C 8/00
[52] U.S. Cl. ................................... 433/172; 433/173
[58] Field of Search ............... 433/172, 173, 174, 177, 433/204, 211

[56] References Cited

U.S. PATENT DOCUMENTS

| | | | |
|---|---|---|---|
| 4,345,901 | 8/1982 | Romagnoli | 433/172 |
| 4,406,622 | 9/1983 | Yoon | 433/172 |
| 4,850,869 | 7/1989 | Steinford et al. | 433/172 |

FOREIGN PATENT DOCUMENTS 2408341 7/1979 France ................................ 433/173

*Primary Examiner*—John J. Wilson
*Attorney, Agent, or Firm*—Henry M. Feiereisen

[57] ABSTRACT

A dental implant prosthesis for use with an oral implant of the type including an implant shaft implanted in a suitably prepared bore in the jawbone of a patient and an abutment connectable to the implant shaft for supporting an external artificial tooth structure, comprises an insert which is insertable in the abutment and a spring-loaded pin which is guided through aligned holes of the insert and abutment and slightly projects outwards from the abutment. The tooth structure is pushed over the abutment, while simultaneously retracting the projecting portion of the pin against the force of the spring to allow the tooth structure to be slid past the pin and eventually to sit upon the gingival area around the bore. The pin snaps back and engages a hole of the tooth structure to securely lock the latter in position.

5 Claims, 2 Drawing Sheets

DENTAL PROSTHESIS FOR USE WITH AN ORAL IMPLANT, AND METHOD OF INSTALLATION

BACKGROUND OF THE INVENTION

The present invention refers to a dental prosthesis for use with an oral implant of the type having an implant shaft inserted in a suitably prepared bore in a jawbone of a patient and an abutment which is connectable to the implant shaft and provided for support of a dental prosthesis or artificial tooth structure.

Dental implants of this type are known in the art. Conventionally, the prosthesis is cemented to the exposed support structure i.e. to the abutment. Cementing, however, is frequently insufficient to attain a secure attachment of the prosthesis. Therefore, it has been proposed to screw the prosthesis to the abutment, with the screw extending slightly slanted inside the prosthesis and being adapted for threaded engagement with the abutment. Such an attachment of the prosthesis to the abutment is sufficient when being able to place the implant shaft in proper alignment with the adjacent teeth. In some patients, however, bone disease may have been progressed to such an extent that available good bone is limited so that the dentist has to shift the placement of the implant shaft to the buccal side or lingual side. In these circumstances the predetermined fixed arrangement of the pin of the prosthesis with the abutment causes a problem when the implant shaft is not installed at an appropriate angle so that the edentulous area could not be restored without showing the prosthesis screw after engagement with the abutment.

In order to overcome this problem, U.S. Pat. No. 4,713,004 describes a dental implant with an implant shaft cooperating with an abutment which is adjustable by means of a ball and socket joint so as allow the dentist to position the abutment in a selected angled relationship with the implant shaft. Apart from using relatively complicated mechanical parts by employing such a ball and socket joint to alleviate the shifted alignment of implant shafts, the artificial dental prosthesis is still required to be cemented or screwed to the abutment.

A general problem of dental implants is the hygiene aspect because the patient is generally in no position to remove or detach the prosthesis properly once the prosthesis is cemented or screwed to the abutment so that the patient has to schedule a visit with the dentist. Moreover, also for the dentist the screwed or cemented attachment of the prosthesis to the abutment requires cumbersome work in order to remove and subsequently restore the dental implant.

A further problem encountered with conventional dental implants is the progressive loosening of the screwed connection between the abutment and the implant shaft.

U.S. Pat. No. 4,406,623 discloses a bone implant fixture for receiving a dental prosthesis, with the implant shaft being comparably of extended length in order to allow secure implantation of the implant fixture in the jawbone. Even though this publication is silent as to the manner of affixing the prosthesis to the abutment or section protruding above the bone, it can be assumed that the prosthesis is cemented or screwed thereto.

SUMMARY OF THE INVENTION

It is thus an object of the present invention to provide an improved dental prosthesis for use with an oral implant, obviating the afore-stated drawbacks.

In particular, it is an object of the present invention to provide an improved dental prosthesis for use with an oral implant, allowing easy removal of the prosthesis by the patient or dentist or replacement thereof, and yet is tightly attached to the implant shaft in the jawbone without showing the prosthesis screw even when the implant shaft is shifted buccally or lingually.

These objects and others which will become apparent hereinafter are attained in accordance with the present invention by providing a hollow abutment which includes a hole at the lingual side thereof for allowing a spring-loaded pin to be inserted therethrough, with one end thereof projecting at the lingual side of the jawbone from the abutment for snapping in a hole of the prosthesis after the latter is placed over the abutment.

According to a preferred embodiment of the present invention, the spring-loaded pin is held in position by an insert which is snugly fitted in the abutment and provided with two opposing holes in alignment with the hole of the abutment. In addition to providing support for the pin, the insert prevents the screw by which the abutment is connected to the implant shaft from loosening as the insert is held by the spring-loaded pin in position and bears against the screw.

By substituting the prosthesis screw for attachment of the prosthesis to the abutment with a spring-loaded pin which is inserted from the lingual side, the prosthesis can be attached without requiring a cementing or screwing of the prosthesis to the abutment. Therefore, the prosthesis can easily be detached for cleaning or replaced if necessary, by simply pushing the pin backwards and snapping out the prosthesis. Moreover, the dentist or surgeon is in a position to utilize the best placement for the implant shaft in the bone regardless of the position of the prosthesis. The prosthesis can be attached to the abutment in proper position, even when the dentist has to shift the implant shaft buccally or lingually because of diseased bone structure.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
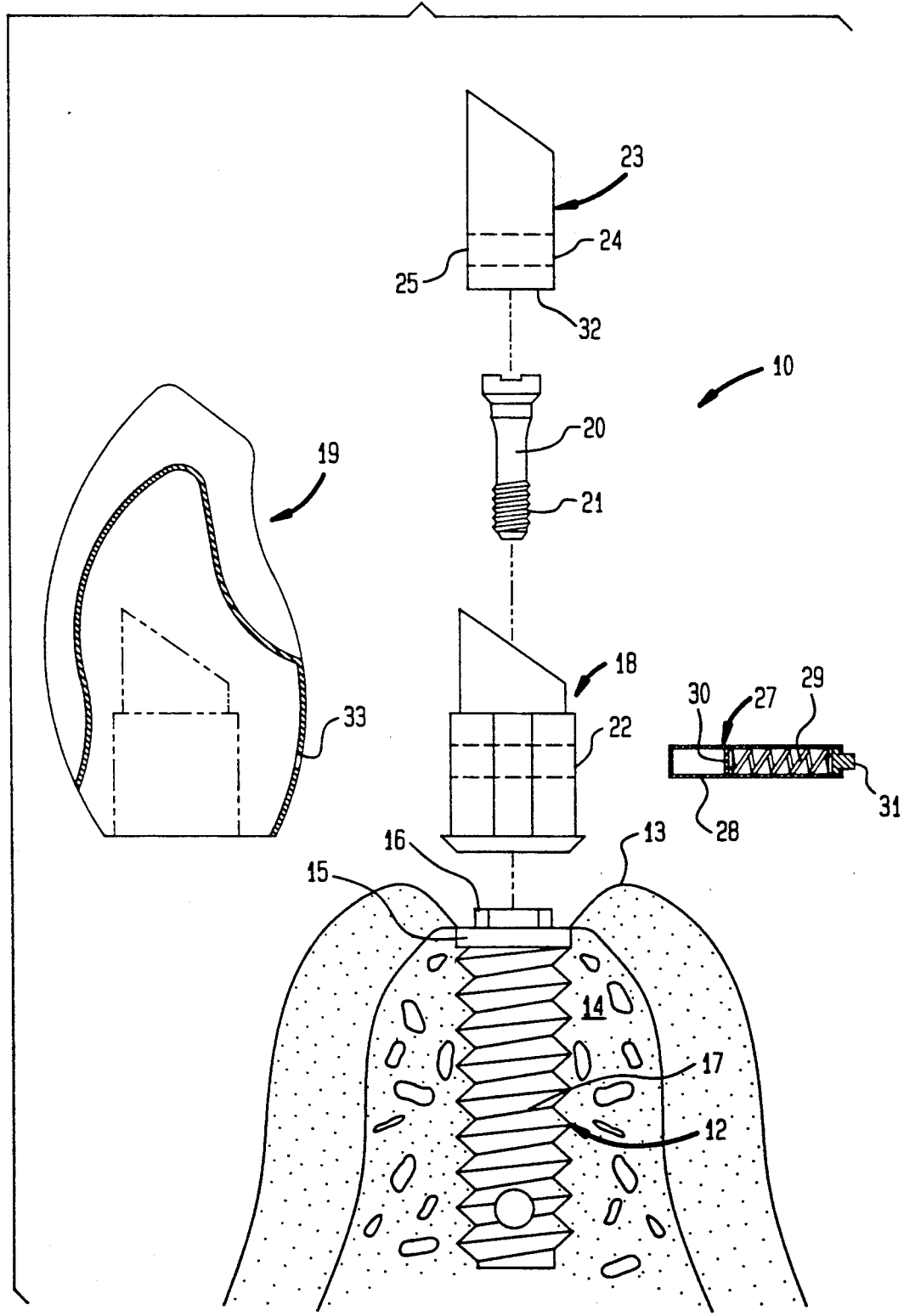
FIG. 1 is a schematic exploded view of a dental implant according to the present invention.

Throughout all the Figures, the same or corresponding elements are always indicated by the same reference numerals unless clearly indicated otherwise.

Referring now to the drawing and in particular to FIG. 1, there is shown an schematic exploded view of a dental implant which is to be placed in an edentulous area of a patient's jawbone and generally indicated by reference numeral 10. The dental implant 10 includes an implant fixture or shaft which is generally designated by reference numeral 12 and buried in a suitably prepared bore or opening 13 in the jawbone 14 of a patient, with the bore 13 extending from the aveolar or gingival crest to an interior region within the jawbone. The implant shaft 12 is provided with a suitably shaped receptacle 15 with a central extension 16 and an exterior screw thread 17 which axially extends from the receptacle 15 at suitable length to allow anchoring of the implant shaft 12 within the bone 14 of the patient. The exterior thread 17 is self-tapping so that the implant shaft 12 enters the prepared bore 13 in the bone 14 during rotation of the implant shaft 12 by means of a tool such as a wrench (not shown). FIG. 1 shows the implant shaft 12 of same diameter over its axial length; however, persons skilled in the art will understand that the shaft 12 may also be tapered over at least part of its axial length.

Partly received in the receptacle 15 and placed over the extension 16 is a hollow abutment which is generally indicated by reference numeral 18 and projects beyond the aveolar crest for supporting a hollow artificial tooth structure or dental prosthesis generally designated by reference numeral 19. The abutment 18 is provided with a screw 20 which has an exterior threaded shaft 21 projecting outwardly for threaded engagement with an internal thread of the implant shaft 12 in order to securely attach the abutment 18 to the implant shaft 12.

Persons skilled in the art will understand that even though it is preferred to have the screw 20 bear with its head portion against the bottom of the abutment 18 when attaching the latter to the implant shaft 12, it is certainly acceptable when the head portion of the screw extends slightly above the bottom of the abutment.

Figure 2:
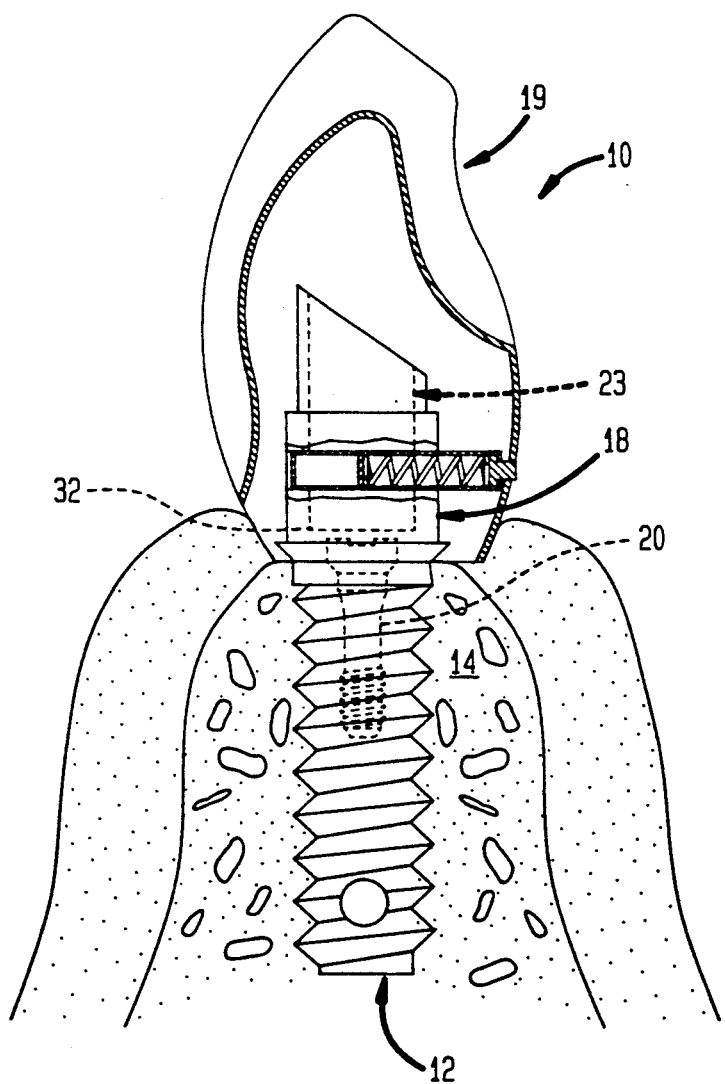
FIG. 2 is a schematic, sectional view of the dental implant in assembled state and installed in a suitably prepared edentulous area of a patient's dentition.

As shown in FIG. 1, the abutment 18 is provided at a suitable location thereof with a hole or opening as indicated at 22. An insert generally designated by reference numeral 23 is provided with opposing holes indicated at 24, 25 and snugly fitted in the abutment 18 in such a manner that the insert holes 24, 25 are in alignment with the hole 22 of the abutment 18 as shown in FIG. 2. Suitably, the insert 23 is a cast member which is waxed and polished before being inserted in the abutment 18.

Guided through the aligned holes 22, 24, 25 of the insert 23 and the abutment 18 is a spring-loaded pin which is generally designated by reference numeral 27 and includes a generally cylindrical housing 28 accommodating a helical compression spring 29 which extends between a stop 30 and a T-shaped plunger 31. As shown in particular in FIG. 2, the spring-loaded pin 27 axially projects from the abutment 18 at the lingual side of the jawbone 14 to allow engagement of the pin 27 with a suitably prepared artificial tooth structure or dental prosthesis which is generally designated by reference numeral 19.

It will be appreciated that a pin of this type is illustrated only by way of example and may be substituted by any other suitable spring-loaded pin or snap element, such as e.g. a pin which includes two cylinders sliding within each other, with one cylinder having a prolongation extending beyond the abutment and being biased by a helical compression spring.

Once the insert 23 is installed in the abutment 18 and suitably secured by the spring-loaded pin 27, the bottom 32 of the insert 23 bears against the head portion of the abutment screw 20 so that the latter is essentially prevented from becoming loose. Although not shown in the drawing, the screw 20 can be further safeguarded against loosening or any rotation by providing the bottom 32 of the insert 23 with an opening which is complementary to the shape of the head portion of the screw 20 so that the bottom 32 of the insert 23, after being placed inside the abutment 18, envelopes the head of the screw 20.

The prosthesis 19 is snapped over the abutment 18, with the plunger 31 of the pin 27 initially being pushed backwards against the force exerted by the spring 29, e.g. by means of a needle or the like so as to allow the prosthesis 19 to be slid past the pin 27 until sitting on the gum line. After passing the pin 27, the plunger 30 is released and forced by the spring 29 against the prosthesis 19 to lock the latter in position. Preferably, the prosthesis 19 is provided at the lingual side with a hole 33 which is in alignment with the holes 22, 24 and engageable by the plunger 31 after the prosthesis 19 is positioned over the abutment 18. In this manner, the prosthesis 19 is tightly secured in position without any possibility of displacement.

Persons skilled in the art will recognize that the use of an insert such as insert 23 may be omitted by providing the abutment internally with a suitable support for the plunger-distant end of the pin. However, the application of an insert is preferred as the abutment screw is kept in place and cannot become loose.

After having described the individual elements of the dental implant, the mode of implantation of the dental implant will now be briefly set forth.

Initially, an incision is made in the gum tissue of the patient and the underlying bone 14 is exposed. A bore 13 of suitable dimension is then drilled in the jawbone for allowing the implant shaft 12 to be screwed in. Thereafter, the abutment 18 is securely mounted to the implant shaft 12 and the insert 23 is securely fitted in the abutment 18. The spring-loaded pin 27 is subsequently inserted through the aligned holes 24, 25 of the insert 23 and the hole 22 of the abutment 18. Subsequently, the prosthesis 19 is slid over the abutment 18, with the plunger 31 of the pin 27 snapping in the suitably located hole 33 of the prosthesis 19 for securing the latter in position. Suitably, the hollow interior of the prosthesis 19 is filled with cement prior to attachment to the abutment 18.

While the invention has been illustrated and described as embodied in a dental implant, and method of installing same, it is not intended to be limited to the details shown since various modifications and structural changes may be made without departing in any way from the spirit of the present invention. For example, the dental implant prosthesis according to the present invention can also be applied for restoring an edentulous area requiring more than one implant.

I claim:

1. A dental implant prosthesis, comprising:
    a implant shaft defining a longitudinal axis and provided for implantation in a prepared bore in a jawbone of a patient, with the jawbone having a buccal and lingual side;
    a hollow abutment including a screw for threaded engagement with said implant shaft in direction of said longitudinal axis of said implant shaft, said abutment extending above said bore for supporting an artificial tooth structure and being provided with a hole at the lingual side; and
    an insert adapted for placement within said abutment and bearing against said screw when being mounted in said abutment to hold said screw in position; and
    resilient locking means for detachably securing said tooth structure to said abutment, said locking means being inserted from the lingual side through said hole in said abutment and snapping in a hole at the lingual side of said tooth structure after placing the latter over said abutment.

2. A dental implant prosthesis as defined in claim 1 wherein said insert is provided with two opposing holes in alignment with said hole of said abutment, said locking means extending through said hole of said abutment and said holes of said insert and having one end projecting beyond said abutment at the lingual side for engagement with the tooth structure.

3. A dental implant prosthesis as defined in claim 1 wherein said resilient locking means is a spring-loaded pin.

4. In a dental implant prosthesis for use with an oral implant of the type having an implant shaft for implantation in a prepared bore in a jawbone of a patient, with the jawbone having a buccal and lingual side; the improvement comprising:

a hollow abutment including a screw for threaded engagement with said implant shaft in direction of said longitudinal axis of said implant shaft, said abutment extending above said bore for supporting an artificial tooth structure and being provided with a hole at the lingual side;

an insert adapted for placement within said abutment and bearing against said screw when being mounted in said abutment to hold said screw in position, said insert being provided with two opposing holes in alignment with said hole of said abutment; and a spring-loaded pin for detachably securing said tooth structure to said abutment, said locking means being guided from the lingual side through said hole in said abutment and said aligned holes of said insert and snapping in a hole of said tooth structure after placing the latter over said abutment.

5. A method of installing a dental implant prosthesis in a jawbone of a patient, comprising the steps of:

preparing a bore in the jawbone having a lingual side and a buccal side;

installing an implant shaft in the bore;

affixing an abutment to the implant shaft by means of a screw, with the abutment extending above the jawbone for providing support for an artificial tooth structure;

placing an insert within the abutment, with the insert bearing against the screw to secure the abutment to the implant shaft;

inserting a resilient locking element through a hole of the abutment, with one end of the locking element projecting at the lingual side outwards from the abutment and with the other end of the locking element being suitably supported in the abutment; and retracting the projecting portion of the resilient locking element and sliding the artificial tooth structure over the abutment, with the locking element snapping back and engaging a lingually disposed hole of the tooth structure for detachably securing the latter in position.

* * * * *